(12) United States Patent
Tahtali

(10) Patent No.: US 9,453,804 B2
(45) Date of Patent: Sep. 27, 2016

(54) METHOD AND APPARATUS FOR GENERATING A REPRESENTATION OF AN INTERNAL STRUCTURE OF AN OBJECT

(71) Applicant: Murat Tahtali, Australian Capital Territory (AU)

(72) Inventor: Murat Tahtali, Australian Capital Territory (AU)

(73) Assignee: NEWSOUTH INNOVATIONS PTY LTD, Sydney (AU)

( * ) Notice: Subject to any disclaimer, the term of this patent is extended or adjusted under 35 U.S.C. 154(b) by 322 days.

(21) Appl. No.: 14/083,530

(22) Filed: Nov. 19, 2013

(65) Prior Publication Data

US 2014/0146942 A1    May 29, 2014

Related U.S. Application Data

(63) Continuation of application No. PCT/AU2012/000540, filed on May 17, 2012.

(30) Foreign Application Priority Data

May 19, 2011    (AU) ................................. 2011901956

(51) Int. Cl.
| | | |
|---|---|---|
| *G01N 23/04* | (2006.01) | |
| *A61B 6/03* | (2006.01) | |
| *A61B 6/00* | (2006.01) | |
| *A61B 6/02* | (2006.01) | |
| *A61B 6/06* | (2006.01) | |

(52) U.S. Cl.
CPC ............... *G01N 23/046* (2013.01); *A61B 6/03* (2013.01); *A61B 6/4007* (2013.01); *A61B 6/4078* (2013.01); *A61B 6/4266* (2013.01); *A61B 6/022* (2013.01); *A61B 6/025* (2013.01); *A61B 6/037* (2013.01); *A61B 6/06* (2013.01); *A61B 6/56* (2013.01); *G01N 2223/419* (2013.01)

(58) Field of Classification Search
CPC .... G01N 23/04; G01N 23/046; A61B 6/547; A61B 6/542; A61B 6/4233
See application file for complete search history.

(56) References Cited

U.S. PATENT DOCUMENTS

| | | | |
|---|---|---|---|
| 4,891,829 A | 1/1990 | Deckman et al. | |
| 2009/0022264 A1 | 1/2009 | Zhou et al. | |
| 2010/0246765 A1* | 9/2010 | Murakoshi ............. | A61B 6/484 378/62 |

FOREIGN PATENT DOCUMENTS

WO    2009115966    9/2009

OTHER PUBLICATIONS

PCT/AU2012/000540, International Search Report, Jul. 2, 2012.
PCT/AU2012/000540, Written Opinion, Jul. 2, 2012.

* cited by examiner

*Primary Examiner* — Hoon Song
(74) *Attorney, Agent, or Firm* — Michael Best & Friedrich LLP

(57) ABSTRACT

The present disclosure provides a method and an apparatus for generating a representation of an internal structure of an object. The method comprises the steps of providing radiation that is arranged to traverse through at least a portion of the object and directing the radiation from different angular directions through at least a portion of the object and towards an optical element, such as a lens or pin-hole. The method also comprises the step of forming a radiation exposure pattern using the optical element, the radiation exposure pattern comprising information indicative of the propagation directions and intensities of component radiation that form the radiation exposure pattern. In addition, the method comprises calculating the representation of the internal structure from the radiation exposure pattern. The method is conducted such that the radiation exposure pattern corresponds to a respective point of view of the object.

20 Claims, 14 Drawing Sheets

METHOD AND APPARATUS FOR GENERATING A REPRESENTATION OF AN INTERNAL STRUCTURE OF AN OBJECT

CROSS-REFERENCE TO RELATED APPLICATIONS

This application is a continuation of International Patent Application No. PCT/AU2012/000540, filed May 17, 2012, which claims priority to Australian Patent Application No. 2011901956, filed May 19, 2011, each of which is incorporated herein by reference in its entirety.

FIELD OF THE INVENTION

The invention generally relates to a method and apparatus for generating a representation of an internal structure and relates particularly, though not exclusively, to a method and apparatus for generating a representation of an internal structure using X-ray radiation.

BACKGROUND OF THE INVENTION

Tomography is a family of imaging techniques that provide a "virtual slice" of an object to reveal internal structure. X-ray computer aided tomography (CAT), usually involves the rotation of an x-ray source and an x-ray detector around an object that is the subject of an inspection or investigation. The object is translated during the investigation. The required mechanical precision may be expensive to achieve, and may require a massive, bulky, gantry.

A CAT scan may involve multiple radiation exposures. Consequently, CAT scans may subject the object to high levels of radiation, which may pose a health risk to animals and humans.

The abovementioned disadvantages limit the use and rate of image acquisition of tomographic and related techniques.

SUMMARY OF THE INVENTION

A first aspect of the present invention provides a method of generating a representation of an internal structure of an object, the method comprising the steps of:

providing radiation that is arranged to traverse through at least a portion of the object;

receiving the radiation from different angular directions by an optical element suitable for the radiation; thereafter forming a radiation exposure pattern using the optical element, wherein a location of the formed radiation exposure pattern relative to the optical element is chosen such that the radiation exposure pattern comprises information indicative of the propagation directions and intensities of component radiation that forms the radiation exposure pattern; and calculating the representation of the internal structure from the radiation exposure pattern;

wherein the method is conducted such that the radiation exposure pattern corresponds to a respective point of view of the object.

In one specific embodiment, the method comprises receiving the radiation from different angular directions by a plurality of optical elements suitable for the radiation; thereafter forming a plurality of respective radiation exposure patterns using the optical elements;

wherein the method is conducted such that the radiation exposure patterns correspond to respective points of view of the object. In this case the method may comprise calculating a single representation of the internal structure or a plurality of representations from at least some, typically all, radiation exposure patterns.

In one embodiment the method comprises detecting the or each formed radiation pattern using a plurality of sensors, such as electronic sensors, that may be positioned in one plane.

The radiation may be any suitable radiation that is arranged to penetrate the object, such as X-ray radiation, gamma ray radiation, terahertz radiation, infrared radiation, or suitable electrons and other particles.

The object may be any suitable object, such as a biological, mechanical object or for example a formation within a ground plane of the Earth.

Embodiments of the present invention have significant advantages. For example, an exposure of the object to the radiation may be reduced compared with known methods, which is of particular advantage if the object is a biological object. As the radiation exposure patterns include information concerning the direction and intensity of the component radiation, the entire structure of the object may be calculated from a single exposure (or very few exposures), which is further facilitated when a plurality of sensors are used. A single pulse of radiation may be sufficient to acquire the radiation exposure patterns from which a "snap shot" representation of the object may be derived.

Further, real time imaging typically is possible and multiple consecutive pulses of the radiation may be used for real time dynamic imaging.

Existing x-ray (or other) imaging systems that give a two-dimensional representation of the internal structures of an object superimposed on each other (for example medical x-ray machines, baggage x-ray machines at airports and the like) may be upgraded to operate in accordance with an embodiment of the present invention.

In an embodiment, each radiation exposure pattern comprises a plurality of regions, each region corresponding to a respective one of a plurality of directions from which the radiation originates.

The step of calculating the representation of the internal structure of the object may comprise generating exposure information indicative of the radiation exposure pattern and processing the exposure information to generate the representation.

In one embodiment, the method comprises generating exposure information indicative of the radiation exposure pattern from which information groups are generated, each group being indicative of the propagation direction and magnitude of a component of the radiation contributing to a respective region. The information groups may be processed to generate the representation. Processing the information groups may comprise at least one of processing the groups using an inverse Radon transform and processing the groups using a derivative thereof.

The or each optical element may comprise, or may be provided in the form of, a radiation focusing element suitable for the radiation, such as a suitable lens. For example, the or each optical element may comprise or may be provided in the form of a kinoform lens, a Fresnel zone plate, or a radiation barrier having an aperture allowing passage of the radiation from one side of the barrier to another side of the barrier, such as a pin-hole.

The step of generating the radiation may comprise directing the radiation through at least a portion of the object from different angular directions that span an angle greater than 10, 20, 30, 40, 50, 60, 70, 80 or even greater than 90 degrees such as more than 130 or even 180 degrees. The radiation may be generated using a radioactive substance.

The method may comprise forming a plurality of the radiation exposure patterns simultaneously. Alternatively, the method may comprise forming a plurality of the radiation exposure patterns sequentially.

In one specific embodiment the method comprises receiving the radiation that traversed through at least a portion of the object by an array of optical elements such that a radiation exposure pattern is formed using, the array of optical elements being positioned at a first position; thereafter moving the array of optical elements relative to the object to at least one successive position; thereafter forming a radiation exposure pattern using the array of optical elements; and calculating the representation of the internal structure from the radiation exposure patterns generated at the first and at least one successive position. The method according to this specific embodiment has the significant advantage that the resolution of the representation of the object may be increased compared to a resolution possible using an array of optical elements that is stationary relative to the object.

The method may also comprise blocking a portion of the generated radiation. This step is typically conducted such that largely or exclusively only radiation that will not contribute to the generation of the radiation exposure patterns is blocked before reaching the object, which has the advantage that an exposure of the object to the radiation may be reduced.

A second aspect of the present invention provides an apparatus for generating a representation of an internal structure of an object, the apparatus comprising:

a source of radiation that is arranged to direct the radiation from different angular directions through at least a portion of the object;

an optical element suitable for the radiation and arranged to form a radiation exposure pattern;

a sensor for sensing the formed radiation exposure pattern; and a processor for processing radiation exposure information and calculating the representation of the internal structure from the radiation exposure pattern;

wherein the apparatus is arranged such that the radiation exposure pattern corresponds to a respective point of view of the object, and wherein the sensor and the optical element are located relative to each other such that the formed radiation exposure pattern comprises information indicative of the propagation directions and intensities of component radiation that forms the radiation exposure pattern.

The source of the radiation typically is external to the object, but may alternatively also form a part of the object. For example, the object may be a radioactive object.

The source of the radiation typically is one of a plurality of sources that may form an array of sources.

In one specific embodiment the apparatus comprises a plurality of the optical elements, such as an array of optical elements, and each optical element is arranged for forming a radiation exposure pattern that comprises information indicative of the propagation directions and intensities of component radiation that forms the radiation exposure pattern, each radiation exposure pattern corresponding to a respective point of view of the object.

The or each optical element may comprise, or may be provided in the form of, a radiation focusing element suitable for the radiation, such as a suitable lens. For example, the or each optical element may comprise or may be provided in the form of a kinoform lens, a Fresnel zone plate, or a radiation barrier having an aperture allowing passage of the radiation from one side of the barrier to another side of the barrier, such as a pin-hole.

In one embodiment, the apparatus is arranged to move the or each optical elements relative to the object form a first position to at least one subsequent position. Further, the apparatus typically is arranged such that radiation exposure patterns are recorded for each position of the or each of optical elements. The apparatus may further comprise a suitable actuator for moving the or each optical elements.

Each radiation exposure pattern may comprise a plurality of regions, each region corresponding to a respective one of a plurality of directions from which the radiation originates.

The apparatus typically also comprises a plurality of sensors that are arranged to detect the radiation pattern. For example, the apparatus may comprise a group of sensors that is associated with the or each optical element.

The apparatus may further comprise a mask having a plurality of bores and that is arranged to block a portion of the generated radiation. The mask typically is arranged such that largely or exclusively only radiation that will not contribute to the generation of the radiation exposure patterns is blocked before reaching the object.

The source of the radiation may be arranged to direct the radiation from different angular directions that span an angle greater than 10, 20, 30, 40, 50, 60, 70, 80 or even greater than 90 degrees such as more than 130 or even 180 degrees.

The source of the radiation may be arranged to generate at least one of, X-ray radiation, gamma ray radiation, terahertz radiation, infrared radiation, electrons and other particles.

A third aspect of the present invention provides a computer program comprising instructions for controlling at least one of a computer and a computational system to processes radiation exposure information and calculating the representation of the internal structure of the object in accordance with the first aspect of the present invention.

In accordance with a fourth aspect, the present invention provides a computer readable medium providing a computer program in accordance with the third aspect of the invention.

The invention will be more fully understood from the following description of specific embodiments of the invention. The description is provided with reference to the accompanying drawings.

DETAILED DESCRIPTION OF EMBODIMENTS OF THE INVENTION

Figure 1:
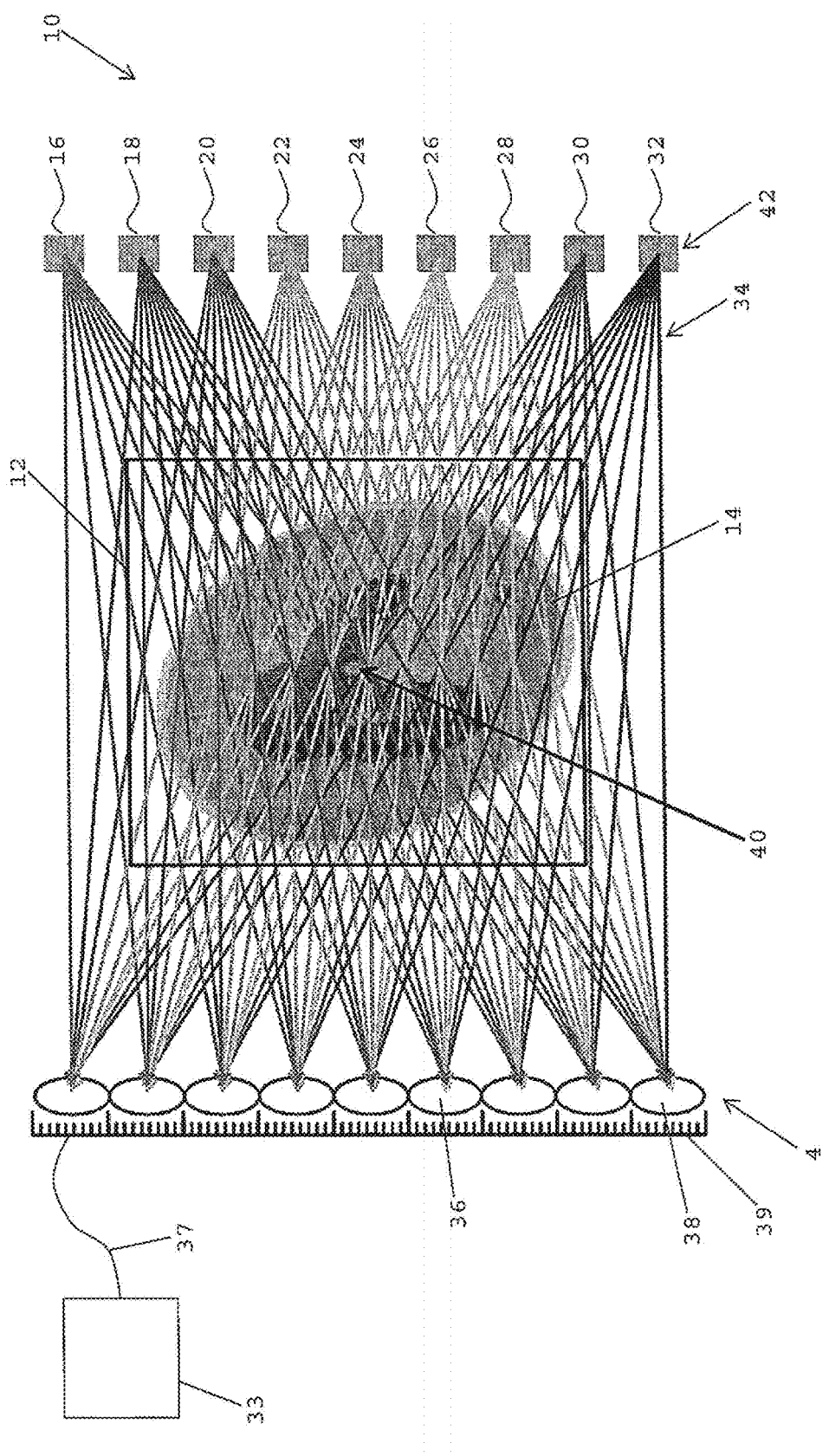
FIG. 1 shows a schematic diagram of an embodiment of an apparatus for generating a representation of an internal structure of an object.
Figure 2:
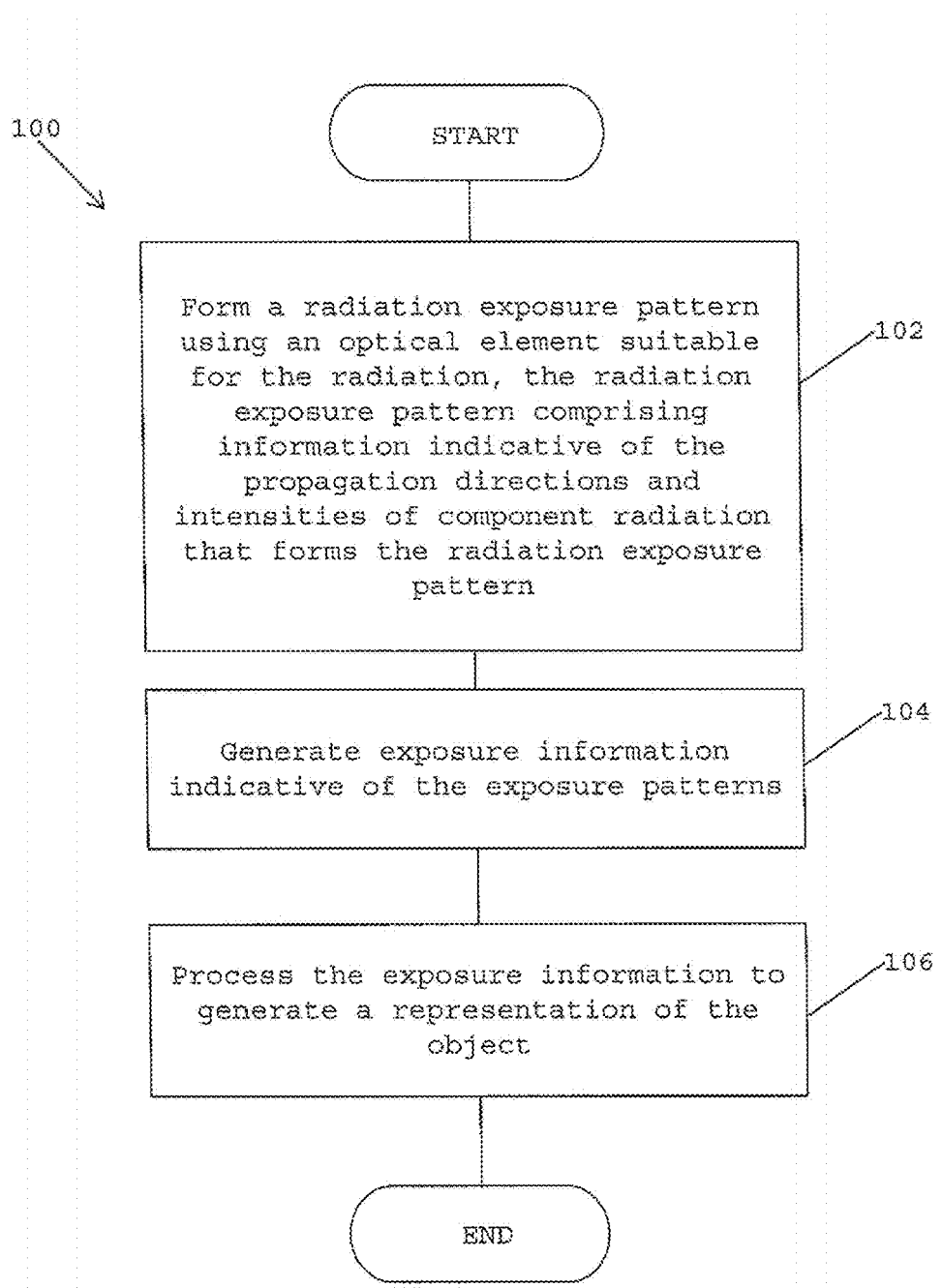
FIG. 2 shows a flow diagram of one embodiment of a method for generating a representation of an internal structure of the object.

FIG. 1 shows a schematic diagram of an embodiment of an apparatus for generating a representation of an internal structure of an object, the apparatus being generally indicated by the numeral 10. The representation may be a tomogram or another representation such as a three dimensional representation. FIG. 2 shows a flow diagram of one embodiment of a method for generating the representation, using an apparatus such as that shown in FIG. 1, the method being generally indicated by the numeral 100.

Figure 15:
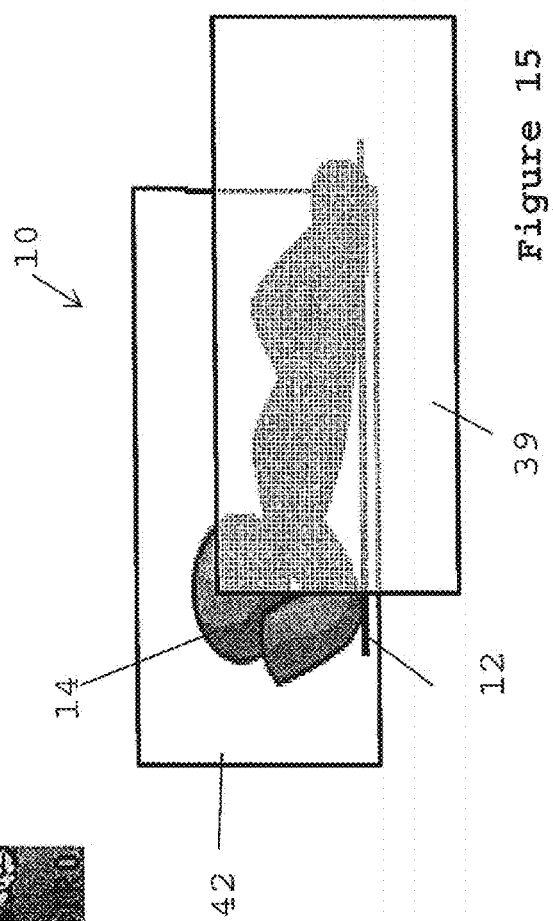
FIG. 15 is a schematic diagram of an example of a person in position for inspection within the device of FIG. 1.

The apparatus 10 has an object receiver 12, which may present a horizontally orientated surface, such as a bench or table surface, on which the object 14 to be imaged is placed. The apparatus, in this but not all embodiments, has a plurality of sources each emitting radiation 34, the sources being indicated by numerals 16 to 32. In this embodiment, the sources are arranged in a two dimensional array (the array is viewed side-on in FIG. 1). FIG. 15 is a schematic diagram of an example of an object or person 14 in position for inspection within the device of object or person 14 in position for inspection within the device of FIG. 1. The apparatus 10 includes an array of sources 42. The radiation from the sources penetrates the object 14 from multiple angles. The radiation is modified as it travels through the object. For example, the radiation may be partially absorbed and/or the phase of the radiation may be modified. In this embodiment, absorption of the radiation is used to facilitate generation of the representation.

Generally, but not necessarily, the sources 16 to 32 simultaneously emit a pulse of radiation so that the patterns are formed simultaneously.

The radiation that has traversed through the object is then manipulated by radiation manipulation (or optical) elements (such as lenses of pin holes), such as those indicated by numerals 36 and 38. The optical elements are arranged, in this but not necessarily in all embodiments, in a two dimensional array (the array is viewed side-on in FIG. 1). The array of optical elements is represented by the plane 39 in FIG. 11. The transparency of plane 29 is for illustrative purposes. The elements are described in more detail below.

The optical elements each produce a radiation exposure pattern (step 102 of the method 100) on a respective sensor of a sensor array 39 disposed behind the array of optical elements. In this embodiment, the sensors are electronic sensors each having a two dimensional array of radiation sensitive elements ("pixels"). The sensors may alternatively be any suitable sensors such as optically read sensors or be regions of, for example, a single or multiple sheets of radiation sensitive film, or another type of sensor.

The sensors are positioned in close proximity of the optical elements (such as within a distance that does not cause radiation from neighbouring optical elements to mix; typically in the order of the distance separating adjacent optical elements). The optical elements and the sensors are positioned relative to each other such that a focused image of the object is not necessarily formed in a plane of the sensors, but instead radiation exposure patterns are formed in a plane of the sensors. Each radiation exposure pattern corresponds to a respective point of view of the object and comprises information indicative of propagation directions and magnitudes of the components of the radiation contributing to the patterns. That is, each pixel of the radiation exposure pattern corresponds to a respective view angle of the object. Each sensor generates exposure information (step 104) in accordance with the radiation exposure pattern formed thereon. The sensor array is in this, but not necessarily all embodiments, a two dimensional array (the array is viewed side-on in FIG. 1).

The sensors are in communication with an exposure information processor 33. The processor 33 processes the exposure information received from the sensor array 39 via, in this but not all embodiments, a data cable 37 connecting the array to the processor to generate the representation (step 106). A wireless connection may replace the data cable, or they may be any other type of communications connector.

The processor may run a program comprising instructions in the form of an algorithm instructing the processor to processes the radiation exposure information indicative of the radiation exposure patterns to generate the representation. The program may be stored on a tangible computer readable medium (for example, a hard disk drive, flash memory, optical or magnetic disk) as may the representation that is generated. Alternatively, the program may be encoded as a signal, such as a signal carried on a network.

Figure 3:
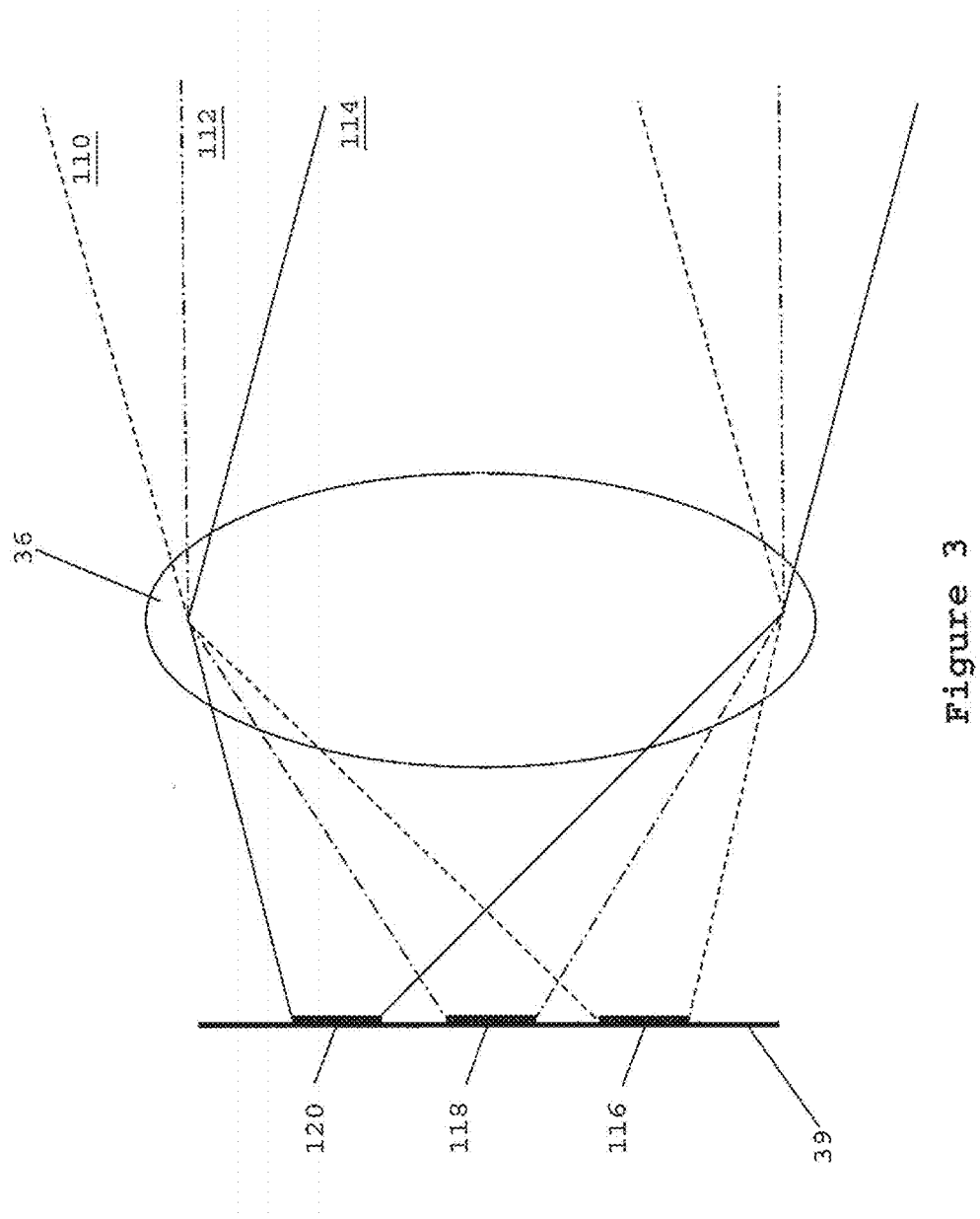
FIG. 3 shows a detail of FIG. 1.

The algorithm selects which group of radiation sensitive elements to use from each sensor. Each group generally, but not necessarily, corresponds to radiation that has originated from a different source. For example, FIG. 3 shows a detail of FIG. 1 around element 36. Radiation from only 3 of the sources is represented by ray boundaries 110, 112 and 114, but it should be understood that the other ray boundaries are omitted only to improve clarity. The ray boundaries are focussed into respective regions 116, 118 and 120, which each illuminate a group of radiation sensitive elements on the sensor array 39. Each region corresponds to a respective one of a plurality of directions from which the radiation originates, when viewing the object. Thus the associated illumination angle of the radiation component that illuminates each region can be determined and processed. Coordinate systems for and local to each region may be defined to facilitate digital mapping of the intensity data in each region.

Example instructions may include an inverse transform such as an inverse Radon transform (IRT), such as one disclosed by Grinber E. et al., *Irregular sampling and the Radon Tranform, Contemporary Meth.*, 2000, 251, and La Riviere et al., *Few-View Tomography using interpolating and smoothing splines with implications for cardiac SPECT, Nuclear Science Symposium*, 1998, published by the IEEE.

After the exposure pattern is recorded and the regions isolated, a series of synthetic cross-sections may be generated.

The sources 16, 18, 20, 22, 24, 26, 28, 30 and 32, in this but not necessarily in all embodiments, are arranged in an array, in this case a two dimensional array (viewed side-on in FIG. 1), generally indicated by the numeral 42. The number of sources is not limited to that illustrated in FIG. 1 and can vary depending on the spatial resolution of the apparatus. The sources each emit radiation which is represented in FIG. 1 by fanning rays generally indicated by the numeral 34. In the context of this specification, the radiation may be any radiation that can at least in part pass through the object—that is any penetrating radiation. The preferred choice of radiation depends on the nature of the object and the investigation, but generally include, for example, x-rays and gamma rays having a wavelength of equal to or less than 10 nm (photon energy of equal to or more than around 120 eV), terahertz radiation, infrared radiation, electrons and other particles.

Using the embodiment of FIG. 1, an object such as a biological object, for example at least a part of either one of an animal and human, may be probed using x-rays and a representation subsequently generated. The sources of FIG. 1 may be x-ray tubes, but any suitable source may be employed such as miniature x-ray generators each comprising a pyroelectric crystal, for example. The sources are each orientated to illuminate with radiation the object when received by the object receiver 12. The object is consequently illuminated from a plurality of directions. In this embodiment each fanning beam bundle corresponds to one of the sources.

The embodiment of FIG. 1, for example, rotates neither a radiation source nor a radiation detector. The whole object may be illuminated. A gantry is not required. This may facilitate dynamic imaging of part or the entire object as desired.

The radiation illuminating the object ("illuminating radiation") spans an angle measured from the centre 40 of the object receiver such that the region to be represented is fully or partially illuminated, to the extent of the sensor plane capturing the traversing radiation. In this embodiment the angle is around 90 degrees, but lesser or greater values may be suitable in some circumstances. In an alternative embodiment, the angle spanned is greater than 15 degrees. Some embodiments have angles of greater than 45 degrees, greater than 90 degrees, greater than 135 degrees, and greater than 180 degrees respectively.

The plurality of optical elements 36, 38 are arranged in an array, in this case a two dimensional array (the array is viewed side-on in FIG. 1). The number of optical elements is not limited to that illustrated in FIG. 1 and can vary depending on the spatial resolution of the apparatus. In this but not all embodiments, each element comprises an imaging element suitable for the radiation. For example, elements 36 and 38 are each optical element in the form of a lens that can focus the radiation 34. Surprisingly, the applicant has determined that suitable lenses may be fashioned for x-ray or gamma ray radiation. The lenses may each be any one of, for example, a kinoform lens, a parabolic refractive x-ray lens, or any suitable lens or optical element. Refractive optics for suitable lenses may be made of low-Z materials such as, for example, beryllium, carbon, aluminium, nickel, and silicon. Alternatively, diffractive lenses such as, for example, Fresnel zone plates (FZPs), may be used. Fresnel zone plates with minimum zone widths of 25 nm and focal lengths of the order of 100 mm for hard x-rays are achievable. Alternatively, grazing angle reflective optics (mirrors) can be used.

Lenses or mirrors may allow for the efficient capture of radiation and consequently the level of radiation required to acquire the pattern may be reduced. Reducing the amount of radiation a human or animal object is exposed to may be highly beneficial in view of health and safety. A single pulse of radiation may be sufficient to acquire the radiation exposure pattern.

The optical elements focus the radiation on the sensors. Due to the extreme shortness of x-ray wavelengths, focal distances may be quite substantial, about 342 mm for a FZP of 384 μm in diameter at 45 keV x-ray energy. In one embodiment, a diameter of 384 μm for the individual FZP cells is chosen to accommodate 16 radiation sensitive elements of 24 μm each under each lens. X-ray sensor arrays of 2084×2084 with 24 μm pixels are commercially available and can be used in the embodiment of FIG. 1.

Existing two-dimensional imaging systems (such as medical x-ray machines, baggage x-ray machines at airports and the like, etc) may be upgraded according to the present disclosure and so produce more complicated representations (such as tomograms, three dimensional and stereoscopic representations).

Figure 4:
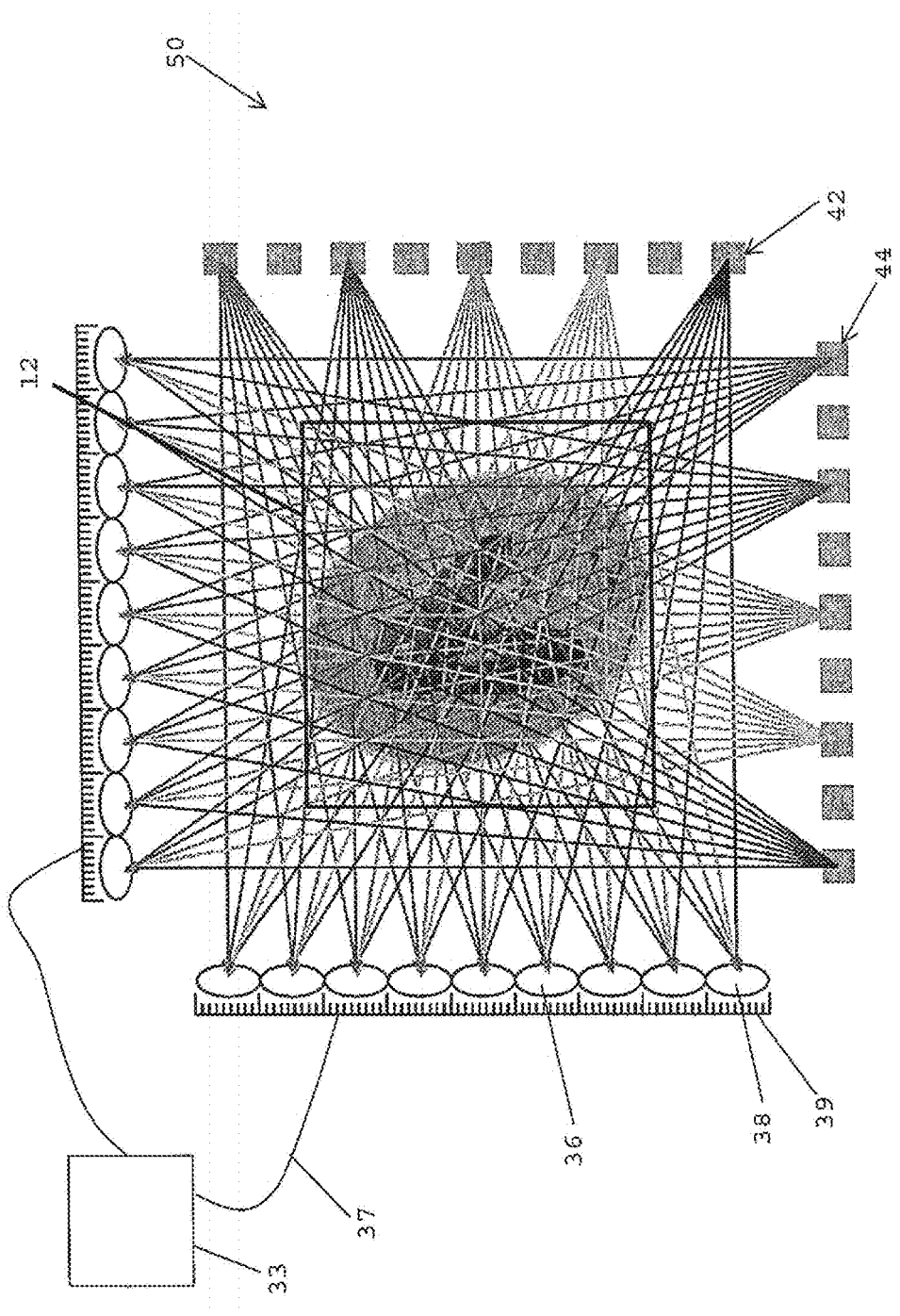
FIGS. 4 and 5 show schematic diagrams of further embodiments of an apparatus for generating a representation of an internal structure of an object.

FIG. 4 shows a schematic diagram of another embodiment of an apparatus for generating a representation of an internal structure of an object, the apparatus being generally indicated by the numeral 50. Parts similar to those illustrated in FIG. 1 are similarly numbered. In this embodiment, the object is illuminated by two transverse arrays of sources (1 in 2 source shown active for clarity of the figure), the arrays being indicated by the numerals 42 and 44. The radiation span angle of FIG. 4 is around (slightly less than) 180 degrees.

In embodiments other than those shown in FIGS. 1 and 4, for example, there may be only one x-ray source.

Figure 5:
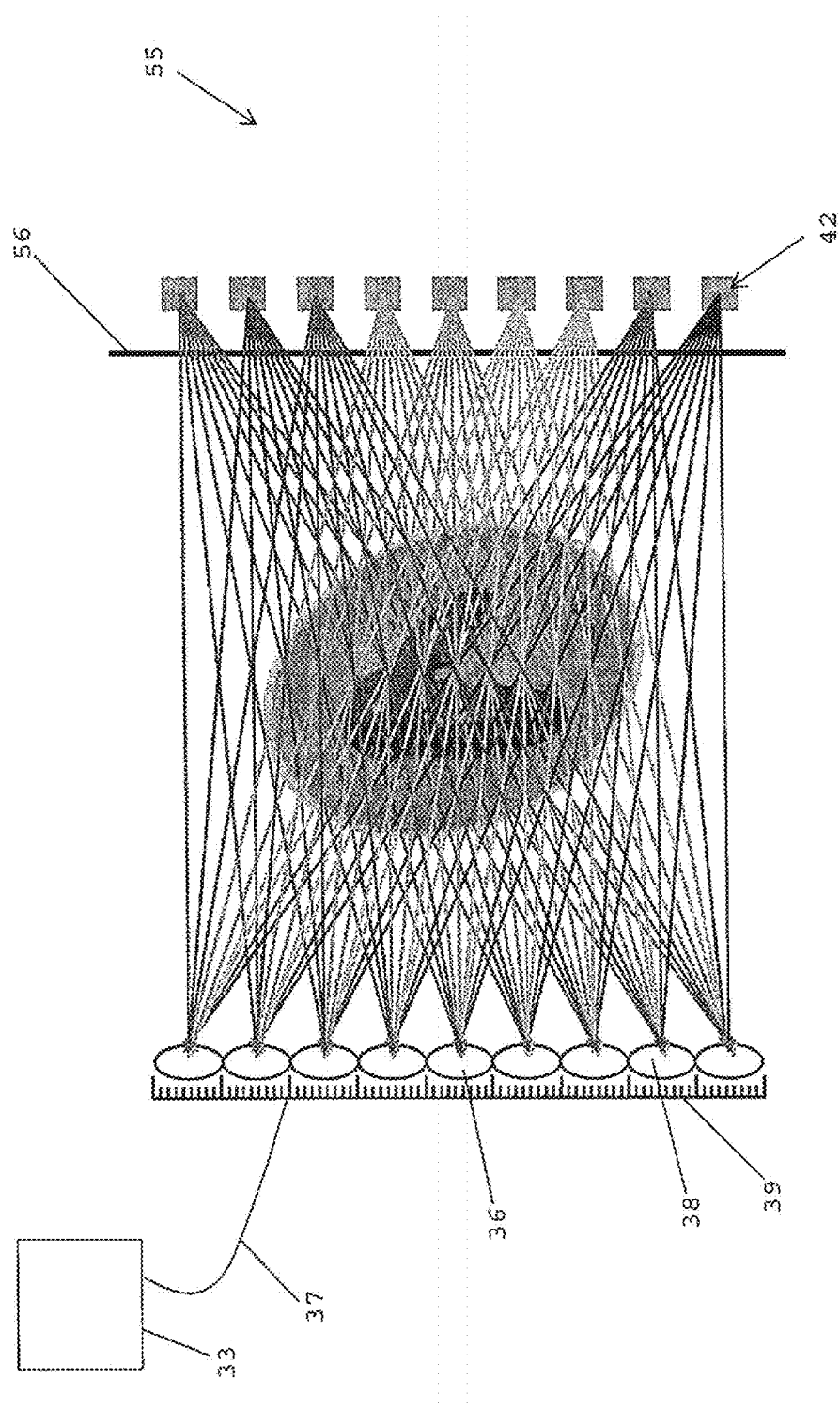
Figure 6:
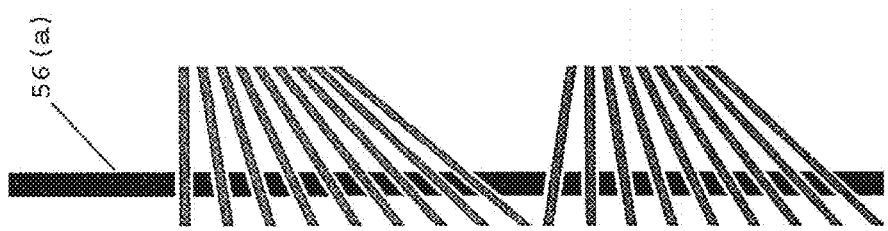
FIGS. 6 (*a*) and (*b*) show a detail of FIG. 5
Figure 6:
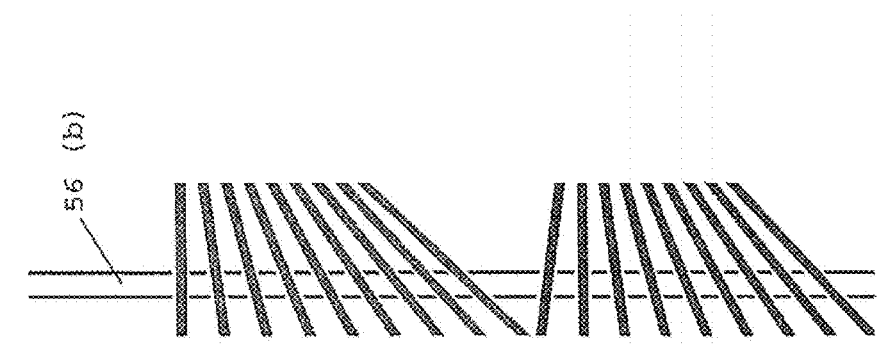

FIG. 5 shows a schematic diagram of a further embodiment of an apparatus 55 for generating a representation of an internal structure of an object and FIG. 6 shows a component of the apparatus 55. The apparatus 55 is related to the apparatus 10 shown in FIG. 1 and to apparatus 50 shown in FIG. 4, but comprises a mask 56. The mask 56 is arranged to block radiation that will not reach the sensors. Radiation that is suitable for penetrating through the object, such as X-ray radiation may be harmful for biological objects (such as humans) when applied in large doses. The mask 56 limits exposure to such radiation, which has clear health benefits.

FIG. 6 (a) shows a first version of the mask 56 (a). In this embodiment the mask 56 (a) is formed from a relatively thick material that absorbs the radiation (such as tungsten, gold or lead in the case of X-ray radiation) and comprises a plurality of bores that are formed in a direction in which the component radiation is directed through the object.

FIG. 6 (b) shows a further variation 56 (b) of the mask. In this case the mask comprises a plurality of two or more component masks that each have bores that are formed in a direction in which the component radiation is directed through the object. If the component masks are thin enough, the bores may be simply bored perpendicular but aligned in the direction in which the component radiation is directed through the object. The component masks are formed from a suitable material that absorbs the radiation (such as tungsten, gold or lead in the case of X-ray radiation).

Figure 7:
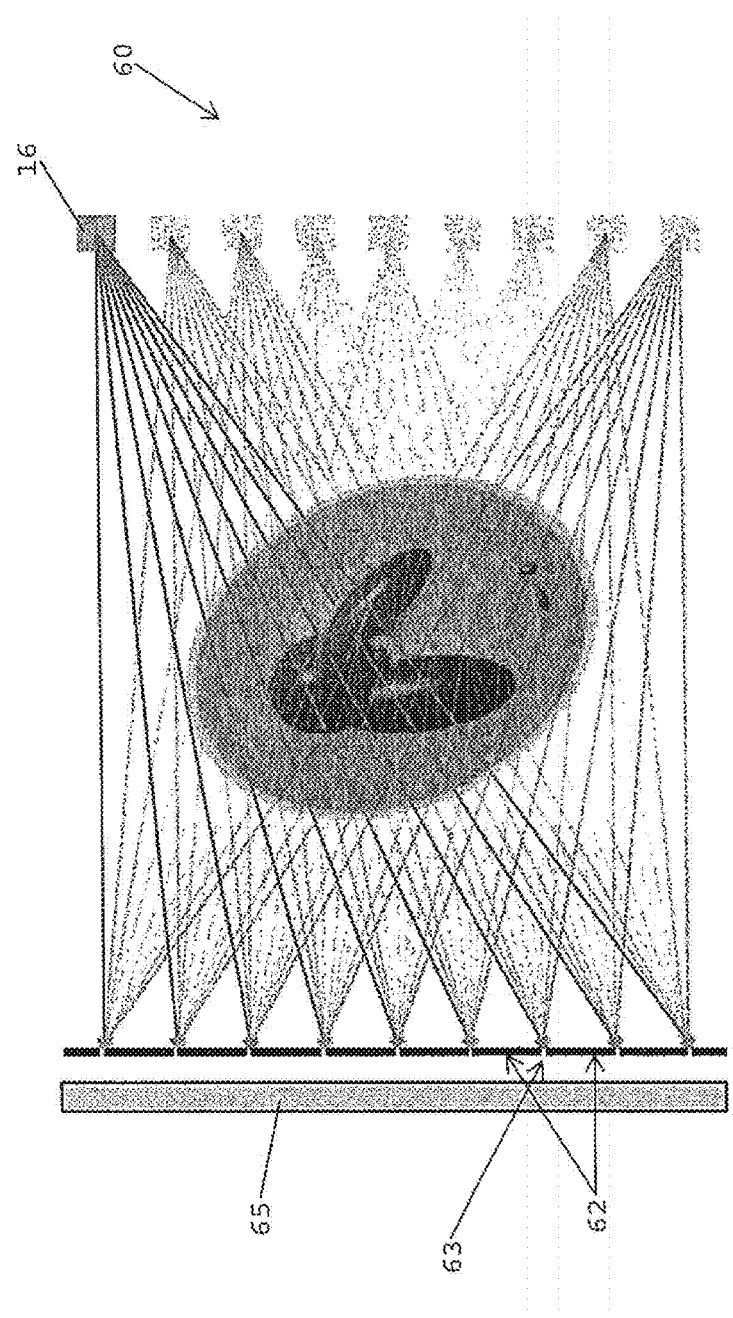
FIG. 7 shows a schematic diagram of yet another embodiment of an apparatus for generating a representation of an internal structure of an object.

FIG. 7 shows a schematic diagram of yet another embodiment of an apparatus for generating a tomogram of an object, the apparatus being generally indicated by the numeral 60. The one x-ray source 16 may be moved so that the object is illuminated from more than one angle by the single source rather than by multiple stationary sources as shown in FIG. 1. Alternatively, the single x-ray source may emit from a wide area so that illumination of the object from multiple angles is achieved without more than the one source. The radiation source may be a single diffuse source.

In still other embodiments, there may be more than the one x-ray source, each being moved or having a wide emission area as described above with respect to an only one source, so that the number of required sources may be reduced. The x-rays may be passed through an x-ray diffusing element.

In the embodiment of FIG. 7, each optical element comprises a radiation barrier portion, such as 62, having an aperture 63 allowing passage of the radiation from one side of the barrier to another side of the barrier. The elements each act similarly to a "pin-hole" in a pin-hole camera and may be described as focusing or imaging elements. The barrier portions may be formed of tungsten, gold or lead sheet, for example. The optimal distance for focused image formation between the pin-holes and the sensors is approximately $f=(d/1.9)^2/\lambda$, where f is the optimal distance, d is the pin-hole diameter and $\lambda$ is the wavelength of the radiation. For a pin-hole of 50 microns, the optimal distance would be about 69 mm, producing an image much larger than the sensor space available behind each pin-hole. As the aim is not to produce a focused image from each pin-hole, but to capture the intensity and the direction of the radiation allowed through each pin-hole, the sensor plane is placed at a distance from the pin-hole array so that it does not cause radiation from neighbouring pin-holes to mix; typically in the order of the distance separating adjacent pin-holes. Behind the array is a sheet of x-ray sensitive film 65 instead of an array of sensors such as that shown in FIG. 1 (although any suitable sensors may be employed). The x-ray film may be developed and subsequently scanned by a scanner, such as a flat bed scanner for example, to generate exposure data that can be sent to and subsequently processed by the processor.

Figure 8:
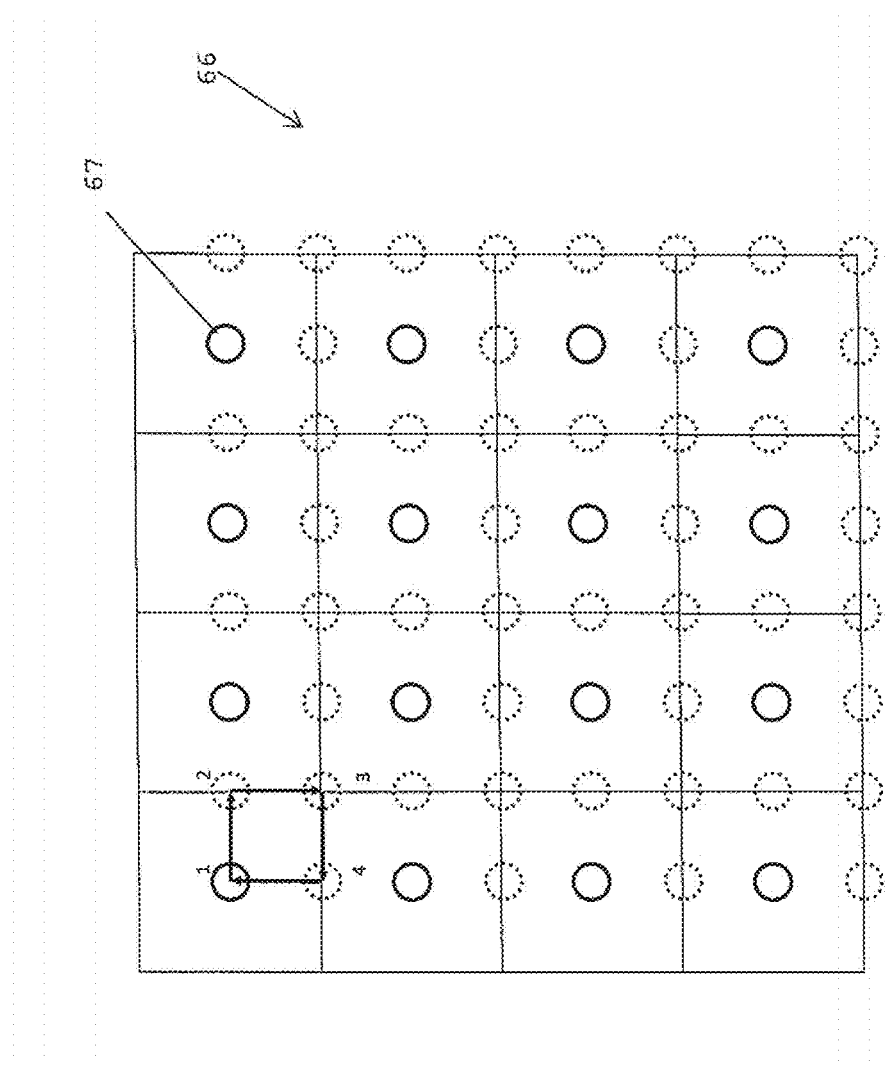
FIGS. 8 and 9 illustrate methods in accordance with embodiments of the present invention.
Figure 9:
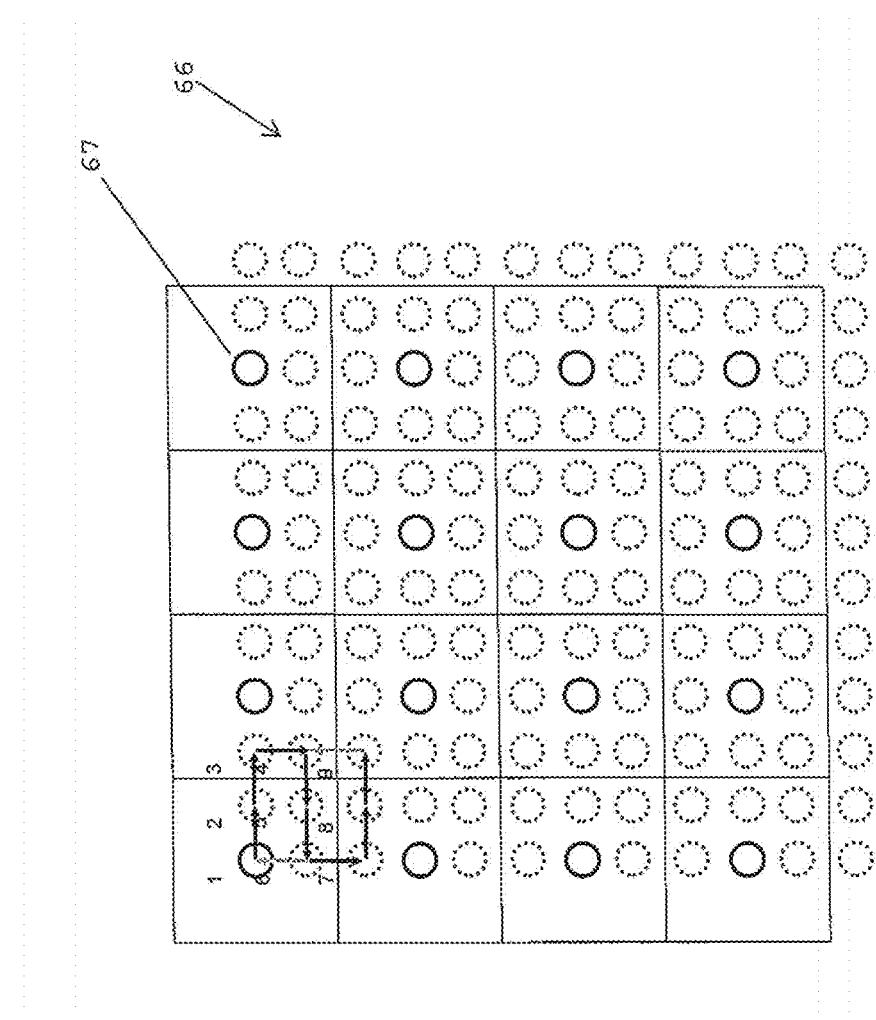

FIG. 8 shows an array 66 of optical elements 67 (such as pinholes or lenslets) that each function as focusing elements. Each optical element 67 functions as a lens and allows the illumination of one or a group of pixels of the sensor array (such as the sensor array 39 shown in FIG. 1). The spacing between the pin-holes limits the number of pixels and consequently the resolution of the radiation pattern. In one embodiment the method of the present invention moves the array 66 such that each pin hole is at a position 1, 2, 3 and 4 as indicated in the top left corner of FIG. 8. At each position the object is exposed to the radiation and radiation patterns are recorded, and the achievable resolution is effectively quadrupled. It is to be appreciated that the pin-hole array 66 may be moved in any suitable positions and radiation patterns may be recorded at these positions. As a further example FIG. 9 illustrates movement of the pin-hole array 66 along a different path from positions 1 to 9 as indicated in the top left corner of FIG. 9. In this example the achievable resolution is increased by a factor of 9. In either example it is beneficial for the achievable resolution if the object is substantially stationary when the series of radiation patterns is recorded.

It is to be appreciated that the array 66 may be moved using any suitable means. For example, the array 66 may be moved using piezoelectric or electro-mechanic actuators, which may be controlled by a suitable computer software.

Figure 10:
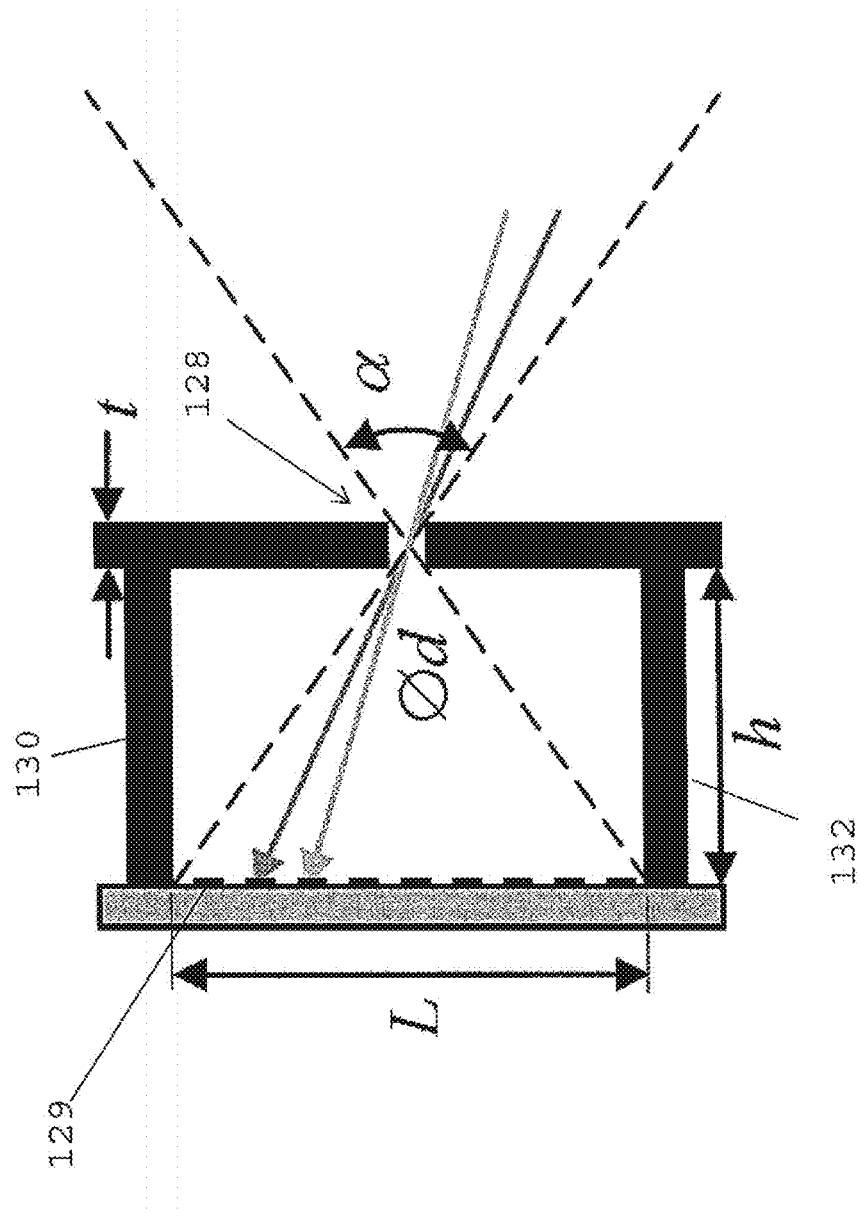
FIG. 10 shows a schematic diagram of rays passing through an aperture.

FIG. 10 shows a pin-hole 128 that is an example of the pinholes of the array 66. The pinhole 128 is used to allow propagation of selected straight rays of the radiation through the pinhole 128 and detection of the radiation at detectors of a detector array 129. The illustration of FIG. 10 is related to that of FIG. 3, but the lens shown in FIG. 3 is replaced with a pinhole 128. The thickness of a metal sheet with a plurality of the pin-holes 128, that may form the array 66, will dictate the view angle α, thus acting as a mask blocking rays inclined more than a certain angle α/2 from normal. From simple geometry, for a straight hole (no taper), this view angle can be calculated as:

$$\alpha = 2\tan^{-1}\frac{d}{t} \qquad \text{Eq. 1}$$

Figure 11:
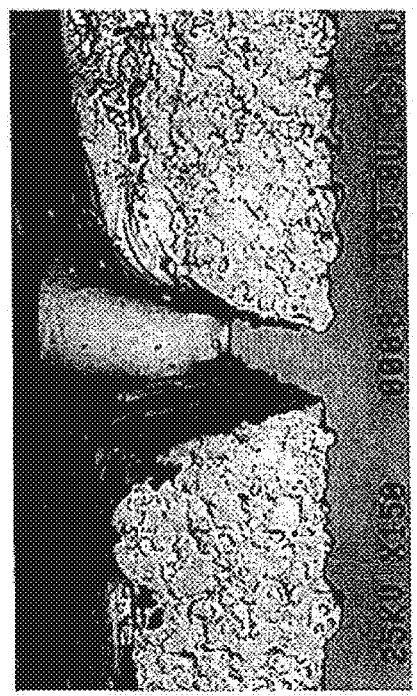
FIG. 11 is an image of an example of a laser perforated channel.

Laser perforation produces tapered holes such as that shown in FIG. 11. In this particular image, a taper slope of about 25/83 can be deduced.

Including the taper slope s, the view angle becomes:

$$\alpha = 2\tan^{-1}\left(\frac{d}{t}+s\right) \qquad \text{Eq. 2}$$

Each pin-hole will form an image of diameter L, therefore the pitch of the pin-hole array should be at least L in order to avoid overlap with the image from neighbouring pin-holes, which can be calculated by:

$$L = 2\frac{hd}{t}+2hs \qquad \text{Eq. 3}$$

where h is the distance between the pin-hole array and the film. For an arbitrary distance h=1 mm, the pitch is calculated as 0.73 mm. Avoidance of image overlap may also be desirable in the case that lenses, rather than pin-holes, are used. Avoidance of image overlap may be enforced by using barriers, made of suitable materials, such as the barriers indicated by the numerals 130 and 132 in FIG. 10. Each optical element may be partitioned by use of the barriers. This may isolate each optical element from its neighbours.

Figure 12:
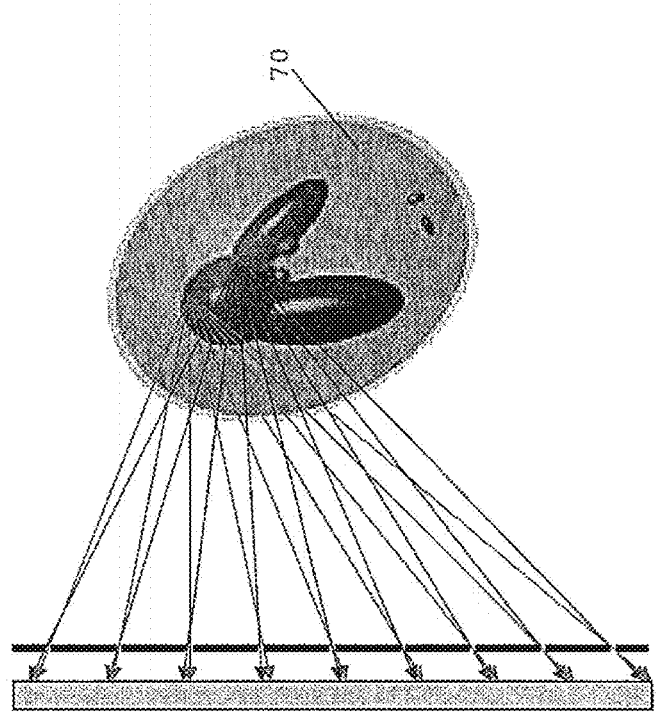
FIG. 12 shows a portion of the apparatus similar to that of FIG. 4 and a radioactive object.

FIG. 12 shows a portion of an apparatus similar to that shown in FIG. 7 and a radioactive object 70. In this example, the object has a radioactive substance which generates the radiation. In other examples, a radioactive substance or source is placed inside the object.

Such an arrangement may be suitable for radioisotope x-ray imaging. For example, the object may be infused with a radioactive substance. A pin-hole/film or other disclosed assembly could surround the object in all directions in the form of a sphere, with an inner shell having pin-holes and an outer shell having the film plate or sensor array. However, for practical reasons, a cubic enclosure with each of its 8 internal faces as a pin-hole and film plate assembly (or equivalent) may be alternatively used. A cylindrical or any other encompassing arrangement may be used.

An aim of ordinary PET in nuclear medicine is solely to image the organ that has been radioactively marked. With this proposed setup, not only the marked organ can be reconstructed in 3D, the surrounding tissues may also be imaged, provided that the absorption of gamma-rays is sufficient enough.

Similarly, an embodiment of the invention may be used to perform a survey of land from an aerial platform, such as an airplane, helicopter, balloon, tower or mountain. The radiation emitted by radioactive minerals in the ground may be detected. Subsequently, any one or more of underground mineral deposits (including the source of the radiation), surface formations, buildings, and any other structures may be reconstructed. Such an embodiment may be equipped with an array of optical elements and sensors as shown in FIG. 12, for example, although any suitable variation or modification such as those taught herein may be used. The array of elements and sensors may be fitted under the belly of an aircraft or balloon and orientated to detect the radiation from the ground. In the case of an aircraft, for example, large areas could be covered by strip scanning of the survey area.

Applications, such as the dynamic and/or real-time imaging of machinery, animals or humans for example, where a radioactive source has been embedded may be realised by some embodiments. A radioactive source emitting radiation in all directions embedded in a structure for testing, for example, may yield more information than a classical x-ray exposure.

In some embodiments, a single sensor plane may be rotated for multiple exposures rather than having multiple sensors placed around the object to be imaged.

In existing PET scanners, the 3D information is reconstructed by timing the coincidence of scintillations on opposite directions, as the annihilation of positrons create 2 gamma photons in opposing directions. Although the timing information may not be used when using an emulsion as the sensor plane (but may be by some electronic sensors), the fact that there may be intensity correlations in opposite directions may be used in bounding portions of the processing algorithms.

It should be noted that it is not always necessary to have the object surrounded by sensor planes in all directions to extract useful 3D information and a compromise coverage can be achieved for practicality reasons.

Figure 13:
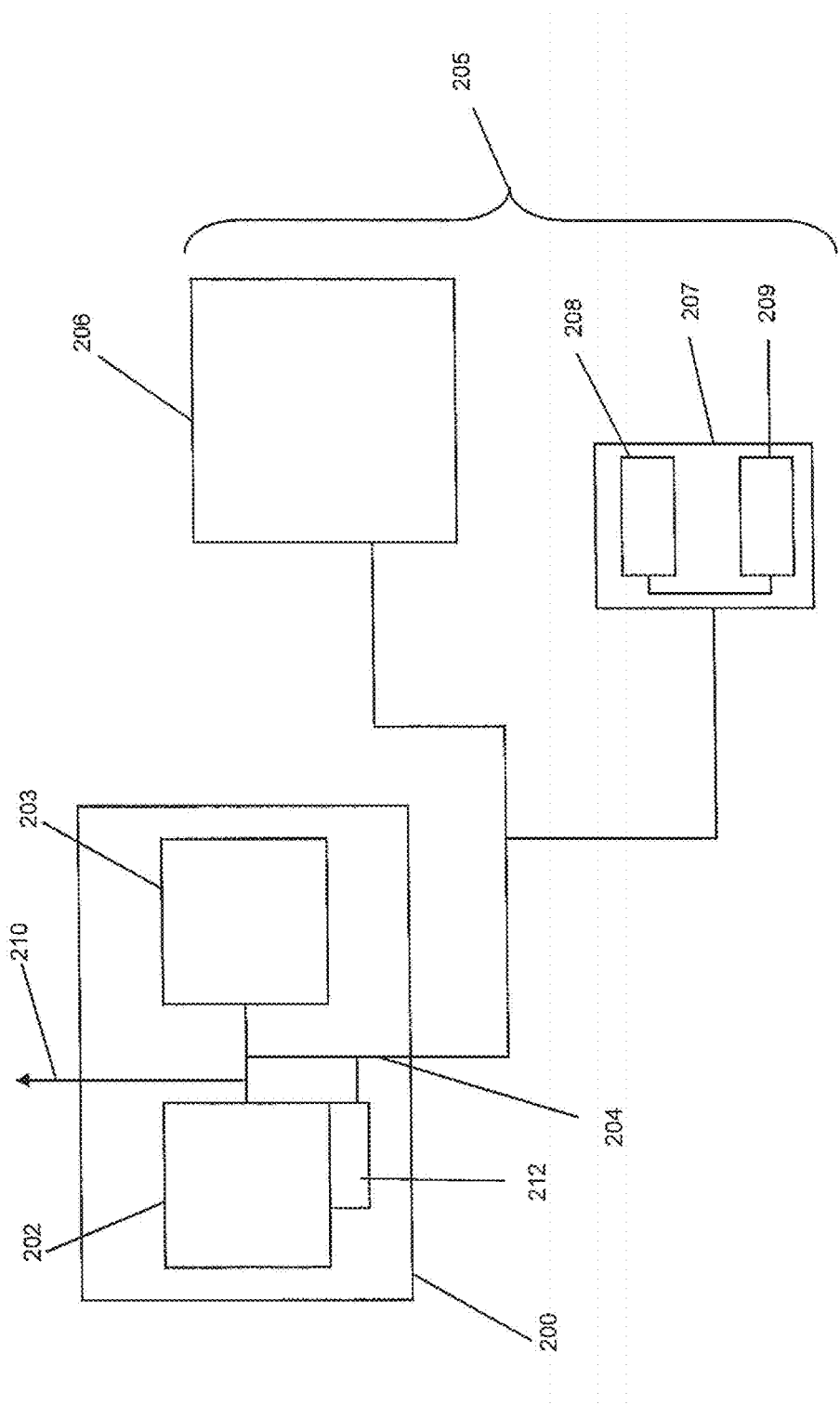
FIG. 13 is a schematic block diagram of an example processor which may be used with the apparatus of FIG. 1 and method of FIG. 2.

FIG. 13 is a schematic block diagram of an example processor which may be used with the apparatus and method described above. The illustrated processor 200, in this embodiment a computing system, comprises a micro processor or central control unit 202 and memory 203. The micro processor or CPU 202 may be arranged to process programme instructions specifying the algorithm and acquired information. Memory 203 is arranged to store programme instructions and data in a known manner. Micro processor or CPU 202 may constitute one or more processing means, such as integrated circuit processors. The memory 203 may comprise any known memory architecture and may include hard disk, IC memory (ROM, PROM, RAM, etc), floppy disks and other types of additional memory such as CD ROM, and any other type of memory. The processor may have a representation generation unit arranged to process the exposure information to generate the representation information. This may be any combination of hardware and/or software. An embodiment has a representation generation unit that may be dedicated hardware unit 212 for faster processing. This may be part of the micro processor or CPU 202 or work with it.

A BUS 204 is provided for communication between the micro processor or CPU 202 and memory 203 and also communication with external components. In this case the external components include a user interface 205. The user interface 205 includes a visual display unit (VDU) 206 for displaying information to a user. The VDU 206 may display information in graphical format (such as a tomogram or other representation) or any other format depending upon the programme instructions being processed by micro processor or CPU 202.

The user interface 205 also includes user input means 207 which in this example include a keyboard 208 (which in this example may be a standard QWERTY keyboard) a mouse 209 and/or a tablet. The mouse 209 may be used to manipulate a graphical user interface (GUI) if a GUI is provided by software running on the computer. A network connection 210 is also provided for connecting to a network which may include a communication network (for example the internet) and other computers/computing systems.

The machine of FIG. 13 may be implemented by any known type of computing hardware such as, for example, an embedded system, a PC, by a number of networked PCs if required to implement a system of this embodiment, by a "mainframe architecture" including a remote computer and user workstations connected to the remote computer, by a client-server architecture, including a client computer accessing a server computer over a network, or by any other computing architecture. This embodiment of the present invention is implemented by appropriate software providing instructions for operation of the computing system hardware to implement the system of the embodiment and implement the method of the embodiment. The computing system need not be connected to a network if this is not required by the software or computer architecture.

Figure 14:
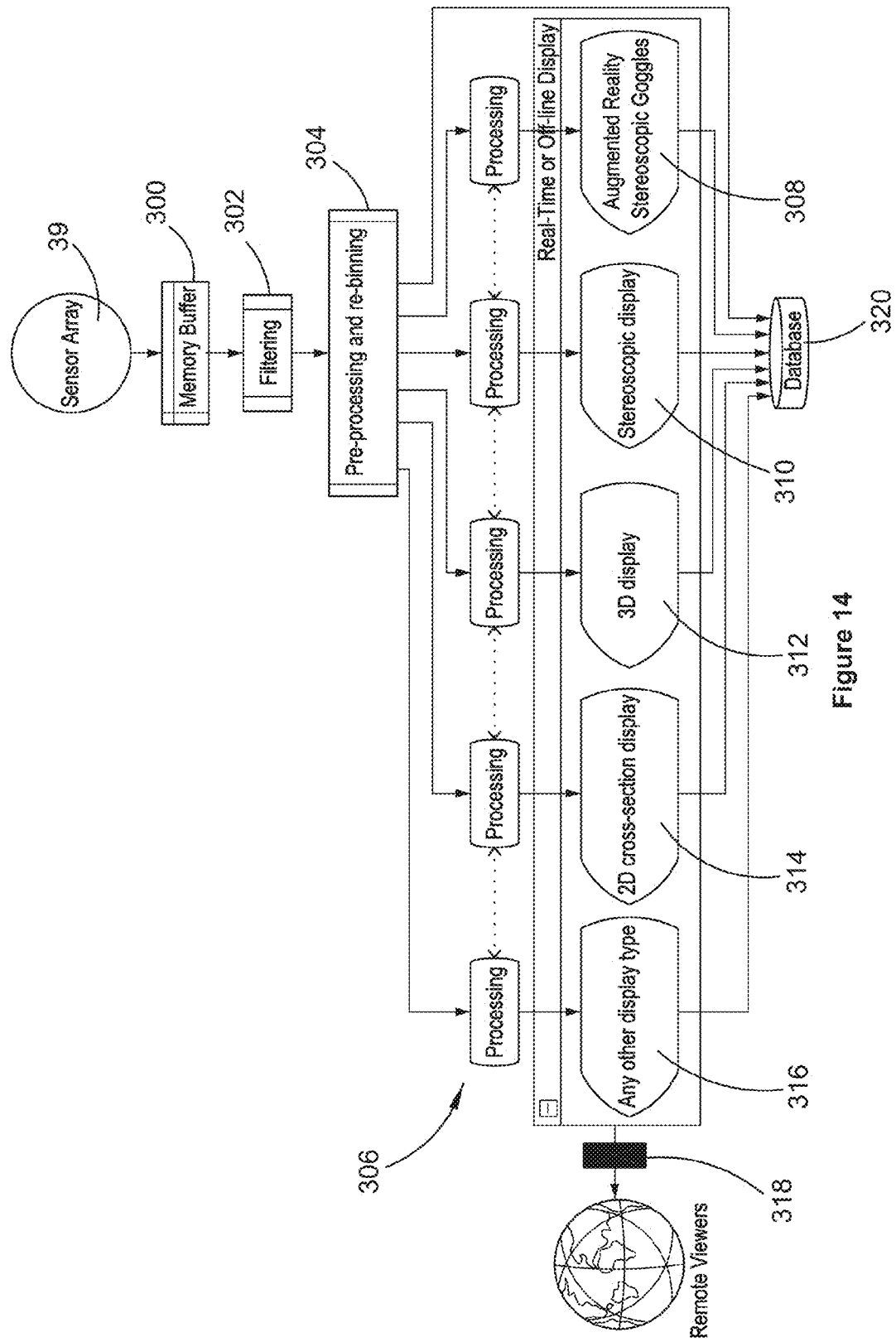
FIG. 14 is a block diagram of processing aspects of an embodiment of the invention.

FIG. 14 shows a block diagram of processing aspects of the method that may be performed using the processor of FIG. 13. The apparatus and/or associated algorithm may comprise:
  a memory buffer unit 300 (which may comprise 203) to capture the sensor data;
  a digital filtering unit 302 to compensate for imaging artefacts caused by various aspects of the radiation and shortfalls of the imaging sensors and electronics;
  a pre-processing unit 304 that prepares the data and forms the information groups;
  a processing unit 306;
  a display unit such as any one of 308 to 316;
  a communication unit 318 for remote viewing; and
  a database 320 to store the data for future access.

The patterns formed on the sensor array behind the array of optical elements have five dimensions of information—x and y (position on the optical elements array), 2 Euler angles (deduced from the x and y position on the groups of radiation sensitive elements behind each optical element) and intensity. The algorithm used to process the data may be alternatively summarised as follows. The pattern may be transmitted as electronic data off-line or in real-time to the processor. The raw radiation exposure pattern is usually re-binned (grouped) into the projection angles that are present. Desired viewing options are selected, such as ROI (Region Of Interest), type of visualization, etc. . . . Proper interpolation is done on missing parts of the data. An inverse transform, such as the inverse Radon transform, may be used to reconstruct the imaged object.

If required, the processed data may be transmitted through appropriate communication channels—such as a network—to remote viewers. Raw data and reconstructed data sets may be catalogued and recorded compressed or uncompressed in a database stored on a storage unit. The dataset may be processed for feature identification for later access or statistical modelling.

There are multiple visualization options as follows.
  The methods and apparatus disclosed may also be used for tomosynthesis. Projections from multiple angles may be used to give an impression of viewing the object in three dimensions. The projections may be cycled through giving an impression of parallax. Stereoscopic viewing may be employed using suitable glasses, for example.
  Augmented reality viewing of the physical object may be achieved, where an internal representation of the object is projected on the visual field of a person wearing stereoscopic goggles. The person may see an image of the inside of the object (perhaps in three dimensions) superimposed on the object when they are looking at the object. Motion and position sensors in the goggles may detect the view point of the viewer and update the superimposed 3D image in real-time, to give the viewers the impression that they have x-ray vision. This type of superimposition can assist surgeons to perform laparoscopic or other non-line of sight surgery, for example. Known augmented reality hardware may use the representations acquired using a method or apparatus disclosed herein.

The imaged object may be viewed in three dimensions from a given observer location similar to watching a 3D movie. This type of viewing would require minimal processing in the form of simply extracting the corresponding projections to the desired view directions. This is not necessarily a 3D reconstruction, but allows 3D viewing of features either by shifting the observer's virtual location or by displaying stereoscopic frames.

A three dimensional (3D) reconstruction of voxels using a two dimensional (2D) and/or 3D inverse transform, such as the inverse Radon transform, may be employed. The reconstructed voxels can also be used to generate stereoscopic image pairs as described above.

3D display in mid-air, using holographic or otherwise projection techniques.

The visualisation techniques may assist medical or industrial applications for dynamic and/or real time inspection and/or intervention. Embodiments may not require translation of the object nor the radiation sources nor detectors. The present invention may be unique in that it can form a representation of the internal mechanism of an object or a beating heart, for example. Other advantages include:
a massive bulky gantry may not be required;
radiation exposure may be reduced;
existing x-ray imaging systems may be upgraded and operated to produce tomograms and other sophisticated representations;
in a positron emission tomography (PET) configuration, not only the organ that is radioactively marked but the surrounding tissues may also be imaged;
multiple visualisation options can be given.

It will be understood to persons skilled in the art of the invention that many modifications may be made without departing from the spirit and scope of the invention. For example, the arrays may be flat, curved stepped, or arranged in any other suitable fashion.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method of generating a representation of an internal structure of an object, the method comprising the steps of:
providing radiation that is arranged to traverse through at least a portion of the object;
receiving the radiation from different angular directions by an optical element suitable for focusing the radiation from the different angular directions onto a, or a respective, sensor; thereafter
forming a radiation exposure pattern using the optical element, wherein a location of the formed radiation exposure pattern relative to the optical element is chosen such that the radiation exposure pattern comprises information indicative of the propagation directions and intensities of component radiation that forms the radiation exposure pattern; and
calculating the representation of the internal structure from the radiation exposure pattern;
wherein the method is conducted such that the radiation exposure pattern corresponds to a respective point of view of the object.

2. The method of claim 1 comprising receiving the radiation from different angular directions by a plurality of optical elements suitable for focusing the radiation; and thereafter
forming a plurality of respective radiation exposure patterns using the optical elements.

3. The method of claim 1 comprising detecting the formed radiation pattern using a plurality of sensors.

4. The method of claim 1 wherein each radiation exposure pattern comprises a plurality of regions, each region corresponding to a respective one of a plurality of directions from which the radiation originates.

5. The method of claim 1 wherein each optical element comprises, or is provided in the form of, a suitable lens.

6. The method of claim 1 wherein the optical element comprises, or is provided in the form of, a radiation barrier having an aperture allowing passage of the radiation from one side of the barrier to another side of the barrier.

7. The method of claim 1 wherein the optical element comprises, or is provided in the form of, a Fresnel zone plate.

8. The method of claim 1 comprising forming a plurality of the radiation exposure patterns simultaneously.

9. The method of claim 1 comprising forming a plurality of the radiation exposure patterns sequentially.

10. The method of claim 1 comprising receiving the radiation that traversed through at least a portion of the object by an array of optical elements such that a radiation exposure pattern is formed using, the array of optical elements being positioned at a first position; thereafter
moving the array of optical elements relative to the object to at least one successive position; thereafter
forming a radiation exposure pattern using the array of optical elements; and
calculating the representation of the internal structure from the radiation exposure patterns generated at the first and the at least one successive position.

11. The method claim 1 comprising blocking a portion of the generated radiation such that largely or exclusively only radiation that will not contribute to the generation of the radiation exposure patterns is blocked before reaching the object.

12. An apparatus for generating a representation of an internal structure of an object, the apparatus comprising:
a source of radiation that is arranged to direct the radiation from different angular directions through at least a portion of the object;
an optical element suitable for focusing the radiation from the different angular directions onto a, or a respective, sensor and arranged to form a radiation exposure pattern;
a sensor for sensing the formed radiation exposure pattern; and a processor for processing radiation exposure information and calculating the representation of the internal structure from the radiation exposure pattern;

wherein the apparatus is arranged such that the radiation exposure pattern corresponds to a respective point of view of the object, and wherein the sensor and the optical element are located relative to each other such that the formed radiation exposure pattern comprises information indicative of the propagation directions and intensities of component radiation that forms the radiation exposure pattern.

13. The apparatus of claim 12 wherein the source of the radiation is external to the object.

14. The apparatus of claim 12 wherein the source of the radiation forms a part of the object.

15. The apparatus of claim 12 comprising a plurality of the optical elements and each optical element is arranged for forming a radiation exposure pattern that comprises information indicative of the propagation directions and intensities of component radiation that forms the radiation exposure pattern, each radiation exposure pattern corresponding to a respective point of view of the object.

16. The apparatus of claim 12 wherein the optical element comprises, or is provided in the form of, a suitable lens.

17. The apparatus of claim 12 wherein the optical element comprises, or is provided in the form of, a radiation barrier having an aperture allowing passage of the radiation from one side of the barrier to another side of the barrier.

18. The apparatus of claim 12 wherein the optical element comprises, or is provided in the form of, a Fresnel zone plate.

19. The apparatus of claim 12 wherein the apparatus is arranged to move the or each optical element relative to the object from a first position to at least one subsequent position and wherein the apparatus is arranged such that radiation exposure patterns are recorded for each position of the or each of optical element.

20. The apparatus of claim 12 comprising a mask having a plurality of bores and that is arranged to block a portion of the generated radiation, the mask being arranged such that largely or exclusively only radiation that will not contribute to the generation of the radiation exposure patterns is blocked before reaching the object.

* * * * *